United States Patent [19]

Sell et al.

[11] Patent Number: 5,241,120
[45] Date of Patent: Aug. 31, 1993

[54] PROCESS FOR THE PREPARATION OF ALKYL 3-CHLOROPHENYL SULFONES

[75] Inventors: Gunther Sell, Kronberg/Taunus; Günther Semler, Kelkheim/Taunus, both of Fed. Rep. of Germany

[73] Assignee: Hoechst Aktiengesellschaft, Frankfurt am Main, Fed. Rep. of Germany

[21] Appl. No.: 856,219
[22] PCT Filed: Nov. 3, 1990
[86] PCT No.: PCT/EP90/01846
  § 371 Date: Jun. 15, 1992
  § 102(e) Date: Jun. 15, 1992
[87] PCT Pub. No.: WO91/07384
  PCT Pub. Date: May 30, 1991

[30] Foreign Application Priority Data
  Nov. 9, 1989 [DE] Fed. Rep. of Germany ....... 3937282

[51] Int. Cl.$^5$ ............................................. C07C 315/04
[52] U.S. Cl. ....................................................... 568/28
[58] Field of Search .................................... 568/28, 35

[56] References Cited

U.S. PATENT DOCUMENTS

3,804,904 4/1974 Bentley et al. .
3,879,472 4/1975 Martin ................................... 568/28
3,886,285 5/1975 Bentley et al. ...................... 424/337
4,675,447 6/1987 Ludvik .................................. 568/28

OTHER PUBLICATIONS

H. Kugita et al, Chem. Abs. 62:6422c–6424d (1965).

Primary Examiner—Marianne M. Cintins
Assistant Examiner—Margaret Page

[57] ABSTRACT

Process for the preparation of alkyl 3-chlorophenyl sulfones of the formula (I), in which $R_1$ and $R_2$ are straight-chain or branched alkyl ($C_1$–$C_4$) groups, which can be identical or different, by reacting alkyl phenyl sulfones of the formula (II), in which $R_1$ and $R_2$ have the meanings given above, with chlorine in sulfuric acid or fuming sulfuric acid at temperatures of about 20 to about 180° C.

9 Claims, No Drawings

PROCESS FOR THE PREPARATION OF ALKYL 3-CHLOROPHENYL SULFONES

The invention relates to a process for the preparation of alkyl 3-chlorophenyl sulfones by reacting alkyl phenyl sulfones with chlorine in sulfuric acid or fuming sulfuric acid.

It is known that, for example, methyl 4-methylphenyl sulfone can be converted to methyl (3-chloro-4-methyl)phenyl sulfone by reaction with chlorine in the presence of antimony(III) chloride without solvents at 85 to 90° C. (H. Kugita et al., Chem. Pharm. Bull. 10, 1001-8, CA 62 6422c). However, the product obtained by this process is contaminated by higher chlorinated byproducts (U.S. 4 675 447, p.1, column 25). Furthermore, the chlorination of methyl 4-methylphenyl sulfone with sulfuryl chloride has been carried out in the presence of metal chlorides, such as iron(III) chloride or antimony(III) chloride at 90 to 92° C. (US 4 675 447). The process results described there could not be confirmed on repeating the work. There is also the fact that large amounts of catalyst are required in this process.

A further possibility for the preparation of alkyl aryl sulfones is the oxidation of the corresponding thioethers (German Offenlegungsschrift 21 60 148), but isomer problems arise during their preparation (D. Chianelli et al. Synthesis 1982 475-8).

There was therefore a need for an improved process for the preparation of alkyl 3-chlorophenyl sulfones in which the disadvantages of the known processes are avoided.

It has now been found that alkyl 3-chlorophenyl sulfones of the general formula (I)

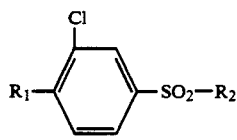

in which $R_1$ and $R_2$ are straight-chain or branched alkyl ($C_1$-$C_4$) groups, which can be identical or different, can advantageously be prepared by reacting alkyl phenyl sulfones of the general formula (II)

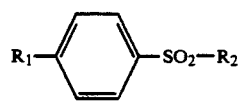

in which $R_1$ and $R_2$ have the meanings given above, with chlorine in sulfuric acid or fuming sulfuric acid at temperatures of about 20 to about 180° C., expediently of about 50 to about 120° C., preferably of about 60 to about 90° C.

The sulfuric acid acting as reaction medium can be used in a concentration of about 50 to 100%, or alternatively in the form of up to 65% strength fuming sulfuric acid. However, sulfuric acid of about 70 to about 96% is preferably used. Working in sulfuric acid of concentrations below 70% can lead to precipitation of the product even during the reaction and thus to consequential inclusions of starting material. Fuming sulfuric acid is less suitable on account of economic reasons and with regard to safety considerations and also offers no advantage with respect to yield and product purity achieved.

The amount of sulfuric acid used is not critical. However, when more than one part by weight of starting material is used per part by weight of sulfuric acid, stirring problems can arise during isolation of the product. When very large amounts of sulfuric acid are used, there is the possibility of yield losses as a result of incomplete isolation of the product during workup. For the optimal course of reaction, 1 to 3, preferably 2, parts by weight of sulfuric acid are generally used per part by weight of starting material.

The chlorination by the process according to the invention is possible at temperatures of about 20 to about 180° C. At temperatures below 50° C. the reaction rate is low, whereas above 120° C products which are more highly chlorinated and discolored are formed. A temperature range of about 50 to about 120° C is expediently used, preferably a range of about 60 to about 90° C.

Furthermore, the chlorination can be carried out at atmospheric pressure and also at superatmospheric pressure, preferably however at atmospheric pressure.

Chlorine is passed in until the starting material has reacted as completely as possible. From the reaction mixture so obtained, the product is precipitated, or the precipitation which has already partially occurred is completed, by addition of water. The product is then isolated by filtration.

An ecologically advantageous way of carrying out the process is to dilute the sulfuric acid to about 70% strength after the reaction by addition of water and to isolate the crystallized-out reaction product from the reaction mixture. A salt-free waste sulfuric acid, which can easily be regenerated, is obtained as mother liquor. The products according to the invention are obtained by this route in high yield and purity.

A further advantage of the present process is that the chlorination proceeds without use of the conventional ring-chlorination catalysts. It can of course also be carried out in the presence of halogenation catalysts, such as iron(III) chloride or antimony(III) chloride.

Apart from by precipitation, the product can also be isolated from the mother liquor by extraction, for example with xylene or halogenated hydrocarbons. It is isolated from the extract by crystallization or distillation.

Alkyl 3-chlorophenyl sulfones, in particular methyl 3-chloro-4-methylphenyl sulfone, are important intermediates for the preparation of crop protection agents (EP 268 795).

EXAMPLE 1

85.1 g (0.5 mol) of methyl 4-methylphenyl sulfone in 160 g of 96% strength sulfuric acid are introduced into a 500 ml glass flask equipped with stirrer, condenser, gas inlet, thermometer and dropping funnel. At 80° C., about 75 g of chlorine are metered in over the course of 6 hours with vigorous stirring. After the reaction is completed, residual hydrogen chloride is eliminated by passing a $N_2$ stream through the flask, 58 g of water are slowly added dropwise and the mixture is then allowed to cool to 20° C. in the course of 2 hours with stirring. The precipitated product is filtered off and washed with about 500 ml of water until free from acid. After drying at 50° C./100 mbar, 96.5 g of 3-chloro-4-methylphenyl methyl sulfone are obtained (content 98.6% by weight, corresponding to a yield of 93.0% of theory, melting point: 91.5° C.).

EXAMPLE 2

92.1 g (0.5 mol) of ethyl 4-methylphenyl sulfone with 160 g of 96% strength sulfuric acid are introduced into a 500 ml glass flask equipped with stirrer, condenser, gas inlet, thermometer and dropping funnel. At 70° C, about 210 g of chlorine are metered in over the course of 6 hours with vigorous stirring. After the reaction is completed, residual hydrogen chloride is eliminated by passing a $N_2$ stream through the flask, 40 g of water are slowly added dropwise and the mixture is then allowed to cool to 20° C. in the course of 2 hours with stirring. The precipitated product is filtered off and washed with about 130 ml of water until free from acid. After drying at 30° C./100 mbar, 100.7 g of 3-chloro-4-methylphenyl ethyl sulfone are obtained (content 98.5% by weight, corresponding to a yield of 90.7% of theory, melting point: 54° C.).

EXAMPLE 3

99.1 g (0.5 mol) of isopropyl 4-methylphenyl sulfone in 180 g of 96% strength sulfuric acid are introduced into a 500 ml glass flask equipped with stirrer, condenser, gas inlet, thermometer and dropping funnel. At 70° C., about 140 g of chlorine are metered in over the course of 6 hours with vigorous stirring. After the reaction is completed, residual hydrogen chloride is eliminated by passing a $N_2$ stream through the flask, 300 g of water are added dropwise and the mixture is allowed to cool to 20° C. in the course of 2 hours with stirring. The mixture is extracted four times each with 200 g of methylene chloride, the combined extracts are washed to neutrality using 5% strength $NaHCO_3$ solution, dried with $Na_2SO_4$ and concentrated on a rotary evaporator. 66.7 g of 3-chloro-4-methylphenyl isopropyl sulfone are obtained (yellowish oil, content 94.3% by weight, corresponding to a yield of 54.1%, $^1$H-NMR ($CDCl_3$): 7.3-7.9 (m, 3H); 3.23 (sp, 6.8 Hz, 1H); 2.47 (s); 1.42 d, 6.8 Hz, 6H).

EXAMPLE 4

85.1 g (0.5 mol) of methyl (4-methylphenyl) sulfone in 150 g of 10.6% strength fuming sulfuric acid are introduced into a 500 ml glass flask equipped with stirrer, condenser, gas inlet, thermometer and dropping funnel. At 65° C., about 120 g of chlorine are metered in over the course of 5 hours with vigorous stirring. After the reaction is completed, residual hydrogen chloride is eliminated by passing a $N_2$ stream through the flask, 69 g of water are added dropwise and the mixture is allowed to cool to 20° C. The precipitated product is filtered off and washed with about 500 ml of water until free from acid. After drying at 50° C./100 mbar, 65.4 g of 3-chloro-4-methylphenyl methyl sulfone are obtained (content 98.5% by weight, corresponding to a yield of 62.9% of theory, melting point: 89-91° C.).

We claim:

1. Process for the preparation of alkyl 3-chlorophenyl sulfones of the general formula (I)

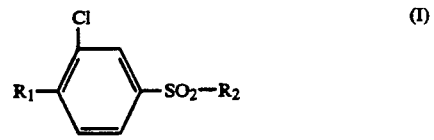

(I)

in which $R_1$ and $R_2$ are straight-chain or branched alkyl $C_1$-$C_4$ groups, which can be identical or different, comprising: reacting an alkyl phenyl sulfone of the formula (II)

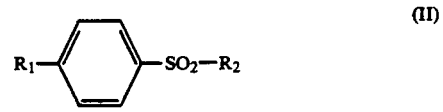

(II)

in which $R_1$ and $R_2$ have the meanings given above, with chlorine in sulfuric acid or fuming sulfuric acid at temperatures of about 20 to about 180° C.

2. Process according to claim 1, wherein the reaction is carried out at temperatures of about 50 to about 120° C.

3. Process according to claim 1 wherein the reaction is carried out at temperatures of about 60 to about 90° C.

4. Process according to claim 1 wherein the reaction is carried out in about 50 to 100% strength sulfuric acid.

5. Process according to claim 1 wherein the reaction is carried out in about 70 to about 96% strength sulfuric acid.

6. Process according to claim 1 wherein the reaction is carried out in up to 60% strength fuming sulfuric acid.

7. Process according to claim 1 wherein the reaction is carried out in 96% strength sulfuric acid and the sulfuric acid concentration after the reaction is reduced to about by addition of water.

8. Process according to claim 1 wherein atmospheric pressure or superatmospheric pressure is employed.

9. Process according to claim 1 wherein $R_1$ and $R_2$ in the general formulae I and II of claim 1 are each a methyl group.

* * * * *

UNITED STATES PATENT AND TRADEMARK OFFICE
CERTIFICATE OF CORRECTION

PATENT NO. : 5,241,120
DATED : August 31, 1993
INVENTOR(S) : Gunther Sell, Gunther Semler It is certified that error appears in the above-indentified patent and that said Letters Patent is hereby corrected as shown below:

In Claim 7, column 4, line 45, after "about", insert --70%--.

Signed and Sealed this

Twenty-first Day of June, 1994

Attest:

BRUCE LEHMAN

*Attesting Officer*    *Commissioner of Patents and Trademarks*